(12) United States Patent
Dufort

(10) Patent No.: US 10,643,092 B2
(45) Date of Patent: May 5, 2020

(54) SEGMENTING IRREGULAR SHAPES IN IMAGES USING DEEP REGION GROWING WITH AN IMAGE PYRAMID

(71) Applicant: INTERNATIONAL BUSINESS MACHINES CORPORATION, Armonk, NY (US)

(72) Inventor: Paul Dufort, Toronto (CA)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 110 days.

(21) Appl. No.: 16/014,801

(22) Filed: Jun. 21, 2018

(65) Prior Publication Data

US 2019/0392243 A1    Dec. 26, 2019

(51) Int. Cl.
 *G06K 9/32*  (2006.01)
 *G16H 30/20*  (2018.01)
 (Continued)

(52) U.S. Cl.
 CPC ........... *G06K 9/3233* (2013.01); *G06K 9/342* (2013.01); *G06K 9/4647* (2013.01); *G06N 3/08* (2013.01);
 (Continued)

(58) Field of Classification Search
 CPC .... G06K 9/3233; G06K 9/4647; G06K 9/342; G06K 2209/05; G06N 7/005; G06N 3/08;
 (Continued)

(56) References Cited

U.S. PATENT DOCUMENTS 6,618,490 B1 * 9/2003 Cham ................ G06K 9/00335
  382/103
6,819,790 B2   11/2004 Suzuki et al.
 (Continued)

FOREIGN PATENT DOCUMENTS

CN     103279933 A    9/2013
CN     106815601 A    6/2017
 (Continued)

OTHER PUBLICATIONS

International Search Report and Written Opinion for Application No. PCT/IB2019/053923 dated Aug. 28, 2019 (10 pages).
 (Continued)

*Primary Examiner* — Qian Yang
(74) *Attorney, Agent, or Firm* — Michael Best & Friedrich LLP

(57) ABSTRACT

A system for determining a region of interest in an image. The system includes a memory and an electronic processor. The electronic processor is configured to create an image pyramid for the image. The image pyramid includes a plurality of layers. For each layer of the image pyramid, the electronic processor is configured to initialize internal states of nodes of a spatial lattice and iteratively update the internal states of the nodes using spatially gated propagation. Each node in the spatial lattice represents a block of pixels in the image and is connected to a node representing a neighboring block of pixels in the image. The electronic processor is also configured to identify the region of interest based on the internal states of the nodes at a convergence of the spatial lattice having nodes representing values included in a first layer of the image pyramid.

24 Claims, 6 Drawing Sheets

(51) Int. Cl.
  *G06N 3/08* (2006.01)
  *G06N 7/00* (2006.01)
  *G06T 7/00* (2017.01)
  *G06K 9/46* (2006.01)
  *G06K 9/34* (2006.01)

(52) U.S. Cl.
  CPC ............ *G06N 7/005* (2013.01); *G06T 7/0012* (2013.01); *G16H 30/20* (2018.01); *G06K 2209/05* (2013.01); *G06T 2207/20016* (2013.01); *G06T 2207/20076* (2013.01); *G06T 2207/20084* (2013.01); *G06T 2207/30096* (2013.01)

(58) Field of Classification Search
  CPC .................. G16H 30/20; G06T 7/0012; G06T 2207/20084; G06T 2207/20016; G06T 2207/20076; G06T 2207/30096
  See application file for complete search history.

(56) References Cited

U.S. PATENT DOCUMENTS

| | | | |
|---|---|---|---|
| 6,910,000 B1* | 6/2005 | Yedidia | ................ G06N 7/005 703/2 |
| 2004/0006450 A1 | 1/2004 | Hale | |
| 2005/0111614 A1 | 5/2005 | Matsuura | |
| 2006/0067573 A1* | 3/2006 | Parr | ................... G06K 9/00201 382/154 |
| 2007/0214133 A1 | 9/2007 | Liberty et al. | |
| 2008/0044080 A1 | 2/2008 | Li | |
| 2008/0292194 A1 | 11/2008 | Schmidt et al. | |
| 2010/0189320 A1 | 7/2010 | Dewaele | |
| 2011/0046927 A1 | 2/2011 | Jeong et al. | |
| 2014/0064580 A1 | 3/2014 | Madabhushi et al. | |
| 2016/0328643 A1 | 11/2016 | Liu et al. | |
| 2017/0124415 A1* | 5/2017 | Choi | ....................... G06N 3/08 |
| 2017/0140263 A1 | 5/2017 | Kaiser et al. | |
| 2017/0243127 A1 | 8/2017 | Zhu et al. | |
| 2017/0277981 A1 | 9/2017 | Zhou et al. | |
| 2017/0372475 A1 | 12/2017 | Gulsun et al. | |
| 2018/0033144 A1 | 2/2018 | Risman et al. | |
| 2018/0068463 A1* | 3/2018 | Risser | ....................... G06T 7/45 |
| 2018/0146935 A1 | 5/2018 | Song et al. | |

FOREIGN PATENT DOCUMENTS

| | | |
|---|---|---|
| CN | 107145910 A | 9/2017 |
| CN | 107832807 A | 3/2018 |

OTHER PUBLICATIONS

Non-Final Office Action from the U.S. Patent and Trademark Office for U.S. Appl. No. 16/014,785 dated Nov. 8, 2019 (32 pages).

\* cited by examiner

SEGMENTING IRREGULAR SHAPES IN IMAGES USING DEEP REGION GROWING WITH AN IMAGE PYRAMID

FIELD

Embodiments described herein relate to segmenting images, such as biomedical images and, in particular, segmenting images using a neural network gating data propagation both in time and space.

SUMMARY

Embodiments described herein relate a new type of neural network unit that combines principles used in recurrent neural networks (RNNs) and convolutional neural networks (CNNs). A RNN receives an input sequence, and reads and processes one element of the sequence at a time. As the RNN processes each element in the sequence, the RNN modifies its knowledge about the sequence, which is stored in the RNN's internal state. A RNN uses some or all of the internal state to either output a second sequence or make a single prediction after it has read all of the input sequence. An example of a RNN is a Long Short-Term Memory (LSTM) neural network that includes one or more LSTM cells. Each LSTM cell stores previous states for the cell, which can be provided to other components of the LSTM neural network. Each LSTM cell includes an input gate, a forget gate, and an output gate. The LSTM was introduced to resolve a problem with RNN training related to vanishing gradients.

A CNN applies filters (kernels) to an input (for example, an image) to make a prediction about the input. In one example, the prediction is which of a set of categories the image belongs to. Filters correspond to features that may be found in the input image. For example, when an image is input to a CNN, the filters are applied to blocks of adjacent pixels in the input image, to produce an intermediate image that indicates how strongly each feature is represented at each position in the image. The content a feature is indicated by the weights of the filter associated with the feature. The weights multiply the pixels included in each block of adjacent pixels. For example, if the input to the CNN is a handwritten digit then the CNN classifies the handwritten digit as a belonging to one of a plurality of categories (in this case the categories are the numbers 1-9). The CNN's classification of the handwritten digit is based on the features of the image that the CNN found to be associated with the digit and how strongly those features indicate that the handwritten digit is one of the numbers 1-9.

Embodiments described herein relate to biomedical image segmentation. Biomedical image segmentation involves identifying boundaries of objects in images, specifically in medical images. Region growing was previously used to identify objects in images. With region growing, a seed pixel is placed somewhere within an object of interest. Once placed in the image, the seed pixel is repeatedly spread to adjacent pixels of similar intensity or brightness. Spreading of the pixel stops when a boundary of the object is reached. In region growing, a boundary may be defined by a drop below a threshold intensity or brightness.

One problem with region growing is that even a tiny connection to an adjacent bright pixel in a medical image can cause the region to spread outside the object of interest. For example, if, as shown in FIG. 1, two bright tissue regions (one tissue region located inside the lung and one tissue region located outside of the lung) are connected by a small, bright tissue fragment, region growing will incorrectly show the two bright tissue regions as belonging to the same mass or object. Accordingly, region growing is often discarded in favor of more sophisticated methods, such as level sets, conditional random fields (CRFs), active contours, and graph cuts.

CNNs discard the primacy of pixel adjacency. Rather, CNNs identify objects that have regularity. An object having regularity allows the CNN to be trained to classify the object as a type of object. However, CNNs may not be able to accurately recognize and segment shapes that are not regular, such as tumor masses, lesions, and the like. Thus, CNNs often fail to accurately determine the boundaries of irregular shapes in medical images, such as shapes that vary in geometry, intensity, or the like.

Accordingly, embodiments described herein provide a technical solution to the problems described above with response to previous solutions for identifying the boundaries of irregularly-shaped objects of interest. Specifically, embodiments described herein incorporate the spatial connectivity of a CNN with temporal gating as used in RNNs to provide a smarter method for segmenting irregular structures in images. In particular, embodiments described herein provide a new type of unit for classifying pixels in an image based on the previous internal states and the current values of the nodes that represent pixels adjacent to the pixel that is being classified. This new type of unit is referred to herein as a gated spatiotemporal unit, which is a gated recurrent unit with spatial awareness normally associated with a CNN. For example, at each time step, each node decides whether or not to update its internal state with the value of its previous internal state or the internal state of one of its neighboring nodes.

Accordingly, the methods and systems described herein provide a neural network that propagates information over both time and space. As compared to merely gating the flow of information over time, gating over both time and space allows a recurrent unit to make decisions about an internal state of a pixel based on the internal states and values of surrounding pixels in the image. Also, in some embodiments, the neural network can propagate information between image resolutions over both time and space.

As described in more detail below, embodiments described herein use machine learning to learn an algorithm. In particular, the network updates until the values associated with internal states converge. In contrast, a single pass network learns a function. As noted above, embodiments herein provide a gated spatiotemporal unit that controls how much information spreads from one pixel to another. As described in more detail below, in some embodiments an image is input to the system, and the system creates an image pyramid including a plurality of layers. Each layer of the image pyramid includes a different number of variables that represent the input image. The base of the pyramid includes a large number of values that represent the image (in other words, the base layer represents the image at a high resolution). At each successive level of the pyramid fewer and fewer values are used to represent the image (in other words, each successive layer represents the image at a lower resolution than the most previous layer). The image pyramid allows information from one part of the image to propagate to a lower resolution and then back to a higher resolution in a different part of the image, in fewer iterations than if the system did not utilize an image pyramid. This is beneficial if, for example, an image with thousands of pixels is input to the system. Such an input could require the system to perform thousands of iterations before generating a prediction. The system performs convolutions using an internal state of the system from a previous time step and the representations of the image in the image pyramid. The results of the convolutional layers are used by the gated spatiotemporal unit to determine values to include in a current internal state of a node in the network. Iterations are performed over the gated spatiotemporal unit until the internal states of the nodes in the network converge. When the internal states of the nodes in the system converge, a probability that each pixel belongs to an object of interest is calculated. In particular, embodiments described herein provide a network for segmenting non-regular structures in medical images that is intelligent about how the data flows over the lattice and learns other factors, such as homogeneity, to determine how to spread the pixel. However, these embodiments may be applicable in domains other than medical imaging segmentation, including, for example, weather prediction, oil and gas modeling, and the like.

For example, one embodiment provides a method for identifying an object of interest in a medical image. The method includes initializing internal states of nodes of a spatial lattice. Each node in the spatial lattice corresponds to a pixel of the medical image and is connected to at least one node representing a neighboring pixel of the medical image. The method also includes iteratively updating, using a neural network, the internal states of the nodes in the spatial lattice using spatially gated propagation. At each iteration, each node updates its internal state based on at least one selected from the group consisting of a value of the node from a previous iteration, a value of a neighboring node from the previous iteration, and a new value of the node. The method further includes identifying the object of interest within the medical image based on the values of the nodes at a convergence of the spatial lattice.

Another embodiment also provides a method for identifying an object of interest in a medical image. However, the method provided by this embodiment includes creating an image pyramid for the medical image. The created image pyramid includes a plurality of layers, each layer includes a plurality of values, and each value represents a block of one or more pixels in the medical image. Each successive layer in the image pyramid includes fewer values than the most previous layer. The method also includes, for each layer of the image pyramid, initializing internal states of nodes of a spatial lattice. Each node in the spatial lattice represents a block of one or more pixels in the medical image and is connected to at least one node representing a neighboring block of one or more pixels in the medical image. The method also includes, for each layer of the image pyramid, iteratively updating, using a neural network, the internal states of the nodes in the spatial lattice using spatially gated propagation. At each iteration, each node updates its internal state based on at least one selected from the group consisting of a value of the node from a previous iteration, a value of a neighboring node from the previous iteration, and a new value of the node. The method further includes identifying the object of interest within the medical image based on the values of the nodes at a convergence of the spatial lattice having nodes representing the values included in a first layer of the image pyramid.

One embodiment provides a system for determining a region of interest in an image. The system includes a memory and an electronic processor. The electronic processor included in the system is connected to the memory and is configured to initialize internal states of nodes of a spatial lattice. Each node of the spatial lattice corresponds to a pixel of the image and is connected to at least one node representing a neighboring pixel of the image. The electronic processor is also configured to iteratively update, using a neural network, the internal states of each nodes in the spatial lattice using spatially gated propagation and identify the region of interest within the image based on the internal states of the nodes at a convergence of the spatial lattice.

Another embodiment also provides a system for determining a region of interest in an image. Like the system of the embodiment described above, the system described in this embodiment also includes a memory and an electronic processor that is connected to the memory. However, the electronic processor of the system provided by this embodiment is configured to create an image pyramid for the image. The image pyramid includes a plurality of layers. For each layer of the image pyramid, the electronic processor is configured to initialize internal states of nodes of a spatial lattice and iteratively update, using a neural network, the internal states of the nodes in the spatial lattice using spatially gated propagation. Each node in the spatial lattice represents a block of one or more pixels in the image and is connected to at least one node representing a neighboring block of one or more pixels in the image. The electronic processor is also configured to identify the region of interest within the image based on the internal states of the nodes at a convergence of the spatial lattice having nodes representing values included in a first layer of the image pyramid.

One embodiment provides a non-transitory computer-readable medium including instructions executable by an electronic processor to perform a set of functions. The set of functions includes initializing internal states of nodes of a spatial lattice. Each node represents a pixel of an image and is connected to at least one neighboring pixel of the image. The set of functions also includes iteratively updating, using a neural network, the internal states of the nodes in the spatial lattice using spatially gated propagation. At each iteration, each node updates its internal state based on at least one selected from the group consisting of a value of the node from a previous iteration, a value of a neighboring node from the previous iteration, or a new value of the node. The set of functions further includes identifying an object of interest within the image based on the values of the nodes at a convergence of the spatial lattice.

Another embodiment also provides a non-transitory computer-readable medium including instructions executable by an electronic processor to perform a set of functions. However, unlike the set of functions in the embodiment described above, the set of functions performed by the electronic processor of this embodiment include creating an image pyramid for an image. The created image pyramid includes a plurality of layers, each layer includes a plurality of values, and each value represents a block of one or more pixels in the image. Each successive layer in the image pyramid includes fewer values than a most previous layer. The set of functions also includes, for each layer of the image pyramid, initializing internal states of nodes of a spatial lattice. Each node of the image pyramid represents a block of one or more pixels in the image and is connected to at least one node representing a neighboring block of one or more pixels in of the image. The set of functions also includes, for each layer of the image pyramid, iteratively updating, using a neural network, the internal states of the nodes in the spatial lattice using spatially gated propagation. At each iteration, each node updates its internal state based on at least one selected from the group consisting of a value of the node from a previous iteration, a value of a neighboring node from the previous iteration, or a new value of the node. The set of functions further includes identifying an object of interest within the image based on the values of the nodes at a convergence of the spatial lattice having nodes representing the values included in a first layer of the image pyramid.

DETAILED DESCRIPTION

Figure 1:
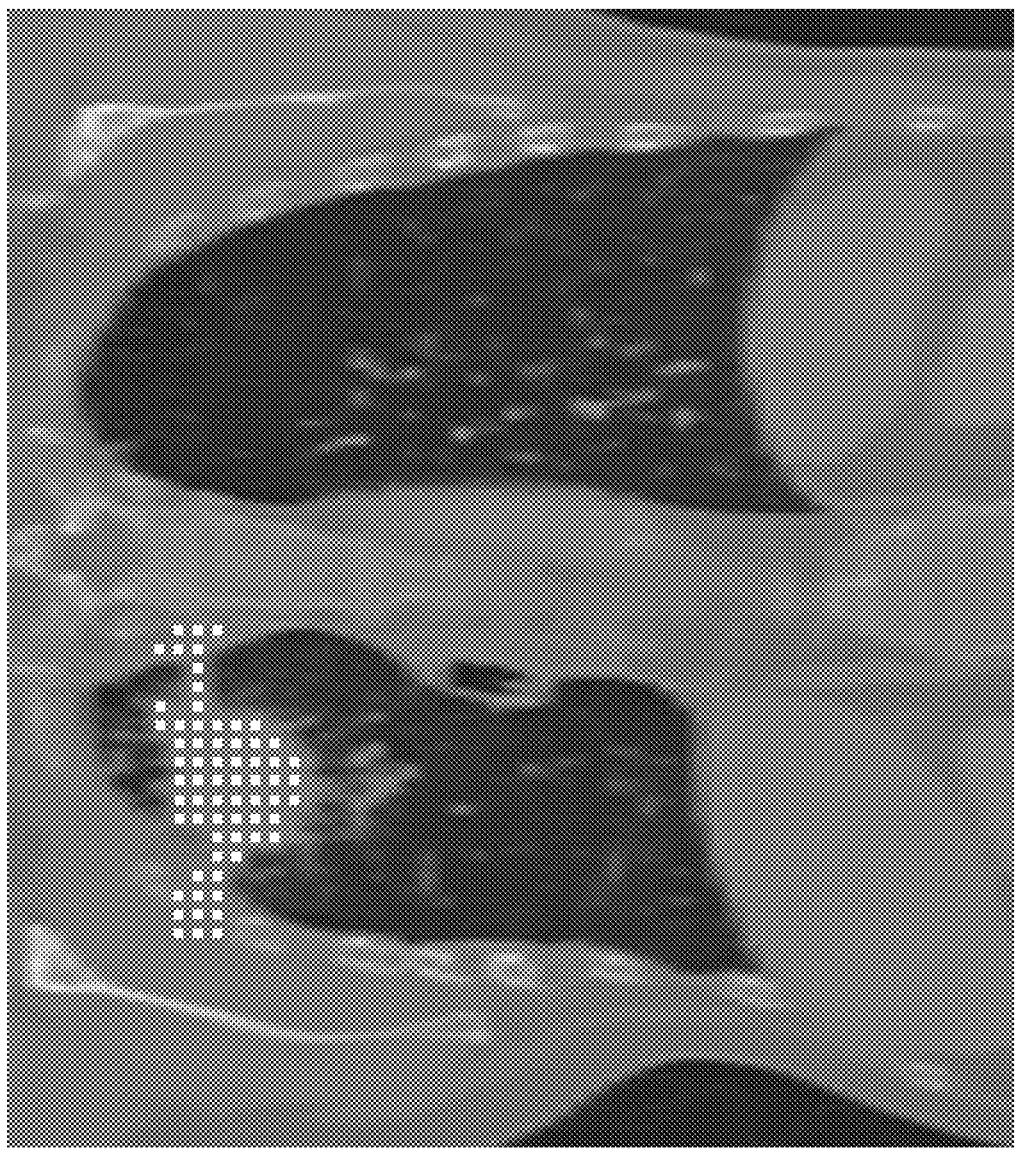
FIG. 1 illustrates a medical image to which region growing has been applied to identify an object of interest.

One or more embodiments are described and illustrated in the following description and accompanying drawings. These embodiments are not limited to the specific details provided herein and may be modified in various ways. Furthermore, other embodiments may exist that are not described herein. Also, the functionality described herein as being performed by one component may be performed by multiple components in a distributed manner. Likewise, functionality performed by multiple components may be consolidated and performed by a single component. Similarly, a component described as performing particular functionality may also perform additional functionality not described herein. For example, a device or structure that is "configured" in a certain way is configured in at least that way, but may also be configured in ways that are not listed. Furthermore, some embodiments described herein may include one or more electronic processors configured to perform the described functionality by executing instructions stored in non-transitory, computer-readable medium. Similarly, embodiments described herein may be implemented as non-transitory, computer-readable medium storing instructions executable by one or more electronic processors to perform the described functionality. As used in the present application, "non-transitory computer-readable medium" comprises all computer-readable media but does not consist of a transitory, propagating signal. Accordingly, non-transitory computer-readable medium may include, for example, a hard disk, a CD-ROM, an optical storage device, a magnetic storage device, a ROM (Read Only Memory), a RAM (Random Access Memory), register memory, a processor cache, or any combination thereof.

In addition, the phraseology and terminology used herein is for the purpose of description and should not be regarded as limiting. For example, the use of "including," "containing," "comprising," "having," and variations thereof herein is meant to encompass the items listed thereafter and equivalents thereof as well as additional items. The terms "connected" and "coupled" are used broadly and encompass both direct and indirect connecting and coupling. Further, "connected" and "coupled" are not restricted to physical or mechanical connections or couplings and can include electrical connections or couplings, whether direct or indirect. In addition, electronic communications and notifications may be performed using wired connections, wireless connections, or a combination thereof and may be transmitted directly or through one or more intermediary devices over various types of networks, communication channels, and connections. Moreover, relational terms such as first and second, top and bottom, and the like may be used herein solely to distinguish one entity or action from another entity or action without necessarily requiring or implying any actual such relationship or order between such entities or actions.

As described above, biomedical image segmentation seeks to identify pixels within an image that represent an object of interest, which allows various calculations and data processing to be performed for the object (for example, volume calculation and the like). Many techniques for performing image segmentation, however, rely on identifying consistent shapes and context. For example, as described above, CNNs excel at recognizing shapes and objects in images that the CNNs have been trained to recognize but CNNs struggle to recognize irregular shapes in images. Accordingly, techniques relying on identifying consistent shapes and context may be ineffective in identifying irregular objects, such as tumor masses, lesions, and the like.

Other techniques rely on pixel spreading to determine the boundaries of an object of interest in an image. As described above, region growing does not rely on regularity but spreads a seed pixel to adjacent pixels until boundaries are identified. Accordingly, the shape of an object of interest does not impact the performance of region growing. However, as shown in FIG. 1, when an object does not have a well-defined boundary (such as when the object is connected to adjacent bright tissue by even a small connection), region growing may improperly grow an object outside of its true boundary.

To solve the deficiencies of the above described techniques, embodiments described herein combine the advantages of CNNs and RNNs in a spatiotemporal unit to improve the identification of the irregular objects in images. In particular, as described in more detail below, embodiments described herein employ spatially gated propagation. Gating involves one piece of a network generating a new state for the system (based on its prior state and newly received information) and a separate piece of the network gating this new state and deciding whether or not the new state will be used and propagated forward in time. As described herein, the most previous internal states of a pixel and the pixel's nearest neighbors are gated and used to determine the internal state of the pixel at a current time step. Therefore, the systems and methods described herein propagate values over both space and time. Additionally, the creation of the above described image pyramid allows the propagation of values over different image resolutions.

Figure 2:
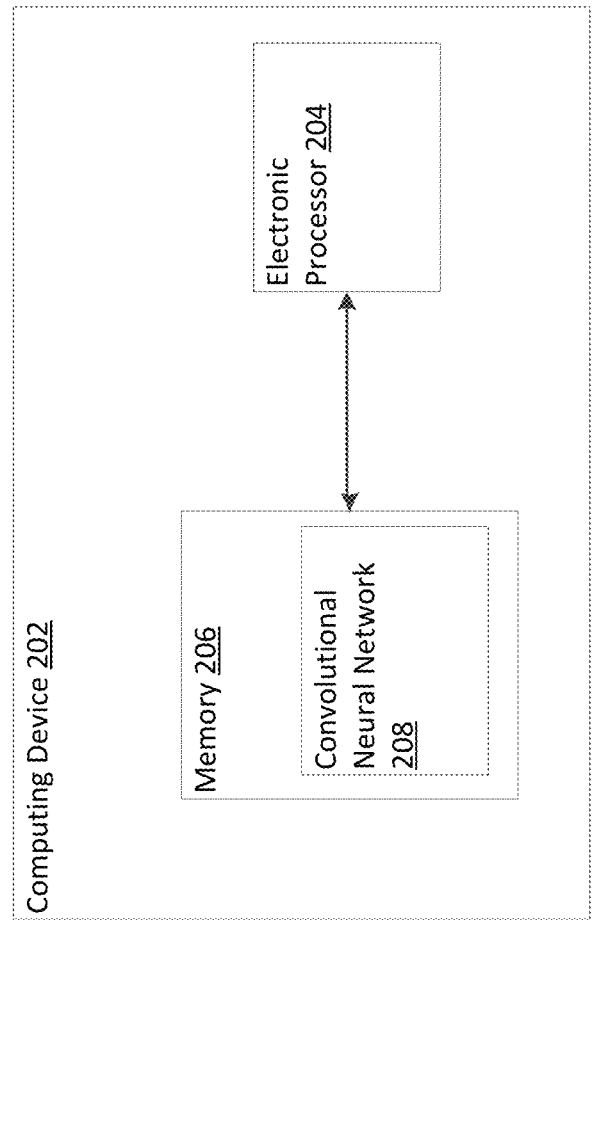
FIG. 2 illustrates a system for determining a region of interest in an image.

FIG. 2 illustrates a system 200 for implementing a neural network. Neural networks are machine learning models that employ one or more layers of nonlinear units to predict an output for a received input. Some neural networks include one or more hidden layers in addition to an input layer and an output layer. The output of each hidden layer is used as input to the next layer in the network (the next hidden layer or the output layer). Each layer of the network generates an output from a received input in accordance with current values of a respective set of parameters.

As illustrated in FIG. 2, the system 200 includes a computing device 202, which includes an electronic processor 204 and a memory 206. The electronic processor 204 and the memory 206 communicate wirelessly, over wired communication channels or buses, or a combination thereof. The computing device 202 may include additional components than those illustrated in FIG. 2 in various configurations. For example, in some embodiments, the computing device 202 includes multiple electronic processors, multiple memory modules, or a combination thereof. Also, in some embodiments, the computing device 202 includes one or more input-output interfaces that allow the computing device 202 to communicate with networks, peripheral devices, and the like.

It should be understood that the functionality described herein as being performed by the computing device 202 may be performed in a distributed nature by a plurality of computing devices located in various geographic locations. For example, the functionality described herein as being performed by the computing device 202 may be performed by a plurality of computing device 202 included in a cloud computing environment. The electronic processor 204 may be a microprocessor, an application-specific integrated circuit (ASIC), and the like. The electronic processor 204 is generally configured to execute software instructions to perform a set of functions, including the functions described herein. The memory 206 includes a non-transitory computer-readable medium and stores data, including instructions that are executable by the electronic processor 204. For example, as illustrated in FIG. 2, the memory 206 stores a neural network 208, which includes a computer program executed by the electronic processor 204.

Figure 3:
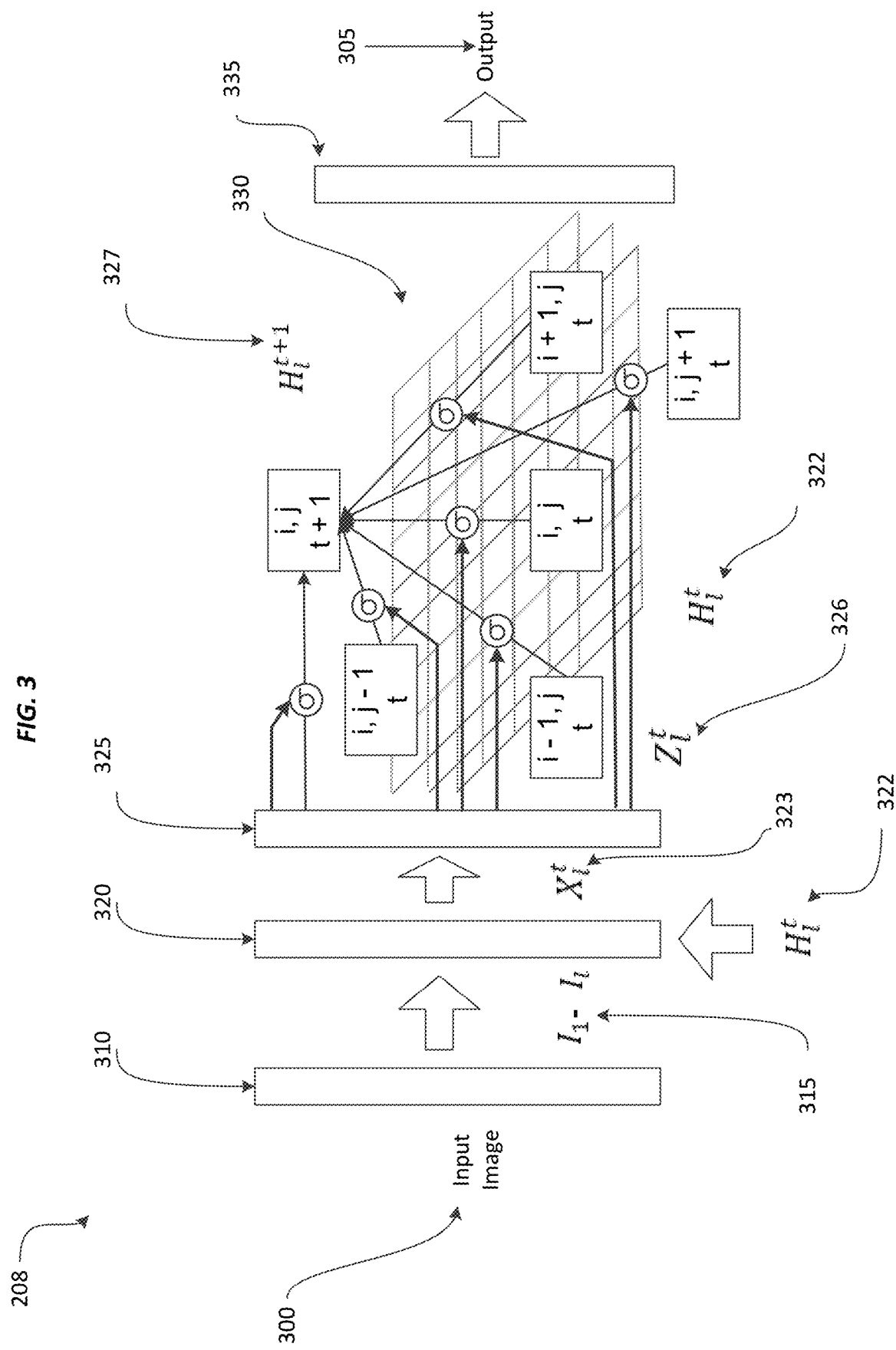
FIG. 3 illustrates a neural network included in the system of FIG. 2.

FIG. 3 illustrates a visual representation of an example of the neural network 208 that the electronic processor 204 executes to perform the methods described herein. As illustrated in FIG. 3, when executed by the electronic processor 204, the neural network 208 provides a machine learning system that receives an input and generates an output 305. As one example, the input includes an image (an input image 300), such as a biomedical image, or another type of multi-dimensional data, and the output 305 similarly includes an image or another type of multi-dimensional data.

As shown in FIG. 3, the input image 300 is input to a first layer 310 of the neural network 208. It should be understood that while the first layer 310 is illustrated as a single layer this is purely for illustrative purposes and the first layer 310 may include any number of layers. In the first layer 310, the neural network 208 may perform a plurality of convolutions on values representing the brightness of each pixel. In other embodiments, the neural network 208 may perform a plurality of convolutions in the first layer 310 to create an image pyramid 315 from the input image 300 ($I_0$), as described below.

The image pyramid 315 is a sequence of tensors ($I_1$–$I_l$) convolved from the input image 300. The tensor produced for l=1 has the same spatial dimensions as the input image 300 ($I_0$), but the tensors halve in size for each subsequent convolution/reduction. Therefore, tensors for each value of l have a different resolution, the tensor $I_1$ has the highest resolution, and the tensor $I_l$ has the lowest resolution. The following equations illustrate the process of creating the image pyramid 315, performed in the first layer 310.

$$I_1 = K_1^I * I_0 \quad (1)$$

$$I_2 = K_2^I * D_1^I * I_1 \quad (2)$$

$$\ldots$$

$$I_l = K_l^I * D_{l-1}^I * I_{l-1} \quad (3)$$

The operator * represents a convolution operation. For example, the equation A*B represents a convolution between an input B and a kernel A.

$I_0$ is a variable that represents the original input image 300. $I_0$ has dimensions $N_0 \times N_0 \times 1$. In other words, the input image 300 has $N_0$ rows, $N_0$ columns, and (because, in this example embodiment, the input image 300 is a greyscale image) one channel.

$I_l$ is a variable that represents an intermediate form of image data (a tensor) produced after one or more reductions are performed on the input image 300 ($I_0$). As described above, when l>1, $I_l$ has a lower resolution than the input image 300 ($I_0$). $I_l$ has the dimensions $N_l \times N_l \times C$, where $N_l = 2^{-(l-1)} N_0$ and C is the number of channels.

$K_l^I$ is a variable that represents a convolution operator (a kernel) that preserves the dimensions of the input image data. The input image data has the dimensions $N_l \times N_l \times C_I$ while the output image data has the dimensions $N_l \times N_l \times C_O$. K may represent the combination of several sequential convolution operations that are arranged as in, for example, AlexNet, DenseNet, or a range of other architectures and the learnable parameters of the convolutional operators.

$D_l^I$ is a variable that represents a convolution operator that reduces the dimensions of the input image data by one half. The input image data has the dimensions $N_{l-1} \times N_{l-1} \times C_I$, while the output image data has the dimensions $N_l \times N_l \times C_O$. Like K, D may represent several sequential convolution operations arranged as in, for example, AlexNet, DenseNet, or a range of other architectures and the learnable parameters of the convolutional operators. However, the convolutional operator D also represents a max-pooling or strided convolution layer that reduces the dimensions of the input image data by half.

The tensor calculated for each level of the image pyramid 315 is fed into a second layer 320. The equation that illustrates the operations performed in the second layer 320 is $$X_l^t = K_l^{IH} * [I_l, H_l^t] \quad (4)$$

Again, the operator * represents a convolution operation, and $I_l$ is a variable that represents an intermediate form of image data (a tensor) produced after one or more reductions are performed on the input image 300 ($I_0$).

[A, B] is a concatenation operation between tensors, for example, the tensors A and B. A concatenation operation performed on two tensors combines the channels included in each of the tensors. For example, if the tensor A has dimensions $M \times M \times C_1$ and the tensor B has dimensions $M \times M \times C_2$, then the output of [A, B] has dimensions $M \times M \times (C_1 + C_2)$.

$H_l^t$ is a tensor 322 that holds an internal state for each node in the spatial lattice at resolution l and time step t. As described above, the internal state of each node in the spatial lattice is updated on each time step. The tensor 322 has the dimensions $N_l \times N_l \times C_H$. Therefore, there are $C_H$ variables describing each block of one or more pixels of the image at resolution l.

$K_l^{IH}$ is a variable that represents a convolution operator that preserves the dimensions of the input image data. The input image data has the dimensions $N_l \times N_l \times C_I$, while the output image data has the dimensions $N_l \times N_l \times C_O$. K may represent the combination of several sequential convolution operations that are arranged as in, for example, AlexNet, DenseNet, or a range of other architectures and the learnable parameters of the convolutional operators.

$X_l^t$ is a variable that represents the results 323 of performing the equation (4). $X_l^t$ has dimensions $N_l \times N_l \times C_X$ and is input to the third layer 325 of the neural network 208.

In summary, equation (4) concatenates the tensor ($I^l$) with the tensor 322 ($H_l^t$) (performs a first concatenation), applies a convolution operator $K_l^{IH}$ to the concatenation (performs a first convolution for a current layer of the image pyramid), and saves the results 323 in tensor $X_l^t$.

The equation that illustrates the operations performed in the third layer 325 is $$Z_l^t = K_l^{L3} * [D_l^X * X_{l-1}^t, X_l^t, U_l^X * X_{l+1}^t] \tag{5}$$

Again, as described above, the operator * represents a convolution operation, and [A, B] is a concatenation operation between tensors, for example, the tensors A and B. Similarly, $K_l^{L3}$ is a variable that represents a convolution operator (a kernel) that preserves the dimensions of the input image data, $D_l^X$ is a variable that represents a convolution operator (a kernel) that reduces the dimensions of the input image data by one half, and $X_l^t$ is a variable representing the result of the equation (4) calculated from the tensor $I_l$, the internal state $H_l^t$, and the kernel $K_l^{IH}$.

$X_{l+1}^t$ is a variable representing the result of the equation (5) calculated from the tensor $I_{l+1}$, the internal state $H_{l+1}^t$, and the kernel $K_{l+1}^{IH}$, and $X_{l-1}^t$ is a variable representing the result of the equation (5) calculated from the tensor $I_{l-1}$, the internal state $H_{l-1}^t$, and the kernel $K_{l-1}^{IH}$.

$U_l^X$ is a variable that represents a convolution operator (a kernel) that upsamples the dimensions of the input image data by doubling the dimensions. For example if the input image data has the dimensions $N_{l+1} \times N_{l+1} \times C_I$, the output image data has the dimensions $N_l \times N_l \times C_O$. Like the convolutional operator K, the convolutional operator U may represent the combination of several sequential convolution operations arranged as in AlexNet, DenseNet, or a range of other architectures and the learnable parameters of the convolutional operations. However, the convolutional operator U may also represent a transposed convolution layer to double the image dimensions.

$Z_l^t$ is a tensor that includes the result of performing equation (5). $Z_l^t$ contains information to be passed to a gated spatiotemporal unit. In summary, equation (5) includes reducing the results ($X_{l-1}^t$) of calculating equation (4) with a tensor representing the input image 300 at a higher resolution ($I_{l-1}$) (a layer of the image pyramid directly below the current layer of the image pyramid) and upsampling the results ($X_{l+1}^t$) of calculating equation (4) from a tensor representing the input image 300 at a lower resolution ($I_{l+1}$) (a layer of the image pyramid directly above the current layer of the image pyramid). Equation (5) also includes concatenating the results of the upsampling with the results of the downsampling, and with the results of calculating equation (4) from a tensor representing the input image 300 at a resolution $I_l$ (performs a second concatenation). The equation convolves the results of the concatenation with the kernel $K_l^{L3}$ (performs a second convolution) and saves the results in the variable Z.

In the first iteration of the neural network 208 merely initializes the internal state for each node included in a spatial lattice of a gated spatiotemporal unit 330 using the output from the third layer 325. Each node includes a vector of values that represent the internal state of the node, and values derived in the image pyramid from the brightness of a block of one or more pixels centered at that node. In each successive iteration, the internal state of each node from the previous iteration is input into the second layer 320 of the neural network 208, via the tensor 322 ($H_l^t$). The process described above is then repeated starting at the second layer 320.

As described above, the neural network 208 includes the gated spatiotemporal unit 330 with a plurality of nodes arranged in a spatial lattice. Each node in this lattice corresponds to a pixel in the input image 300. The gated spatiotemporal unit 330 performs data processing at each of multiple time steps. At each time step, the gated spatiotemporal unit 330 receives a plurality of values. Based on the received values and the values representing the internal state of each node that were gated in the previous time step, the gated spatiotemporal unit 330 determines how to update internal state of each node at the current time step. As will be described in more detail below, the gated spatiotemporal unit 330 determines how to update the internal state of each node by deciding, for each node in the lattice, whether to maintain the internal state of the node at a previous time step, set the node's internal state to a value representing the internal state neighboring node from a previous time step, or generate a new internal state for the node.

The following equation is an example of a computation used to determine the internal state $H_l^{t+1}$ 327 of a node included in the lattice of the gated spatiotemporal unit 330 at the current time step and is distributed over seven lines (labeled I-VII) for ease of interpretation.

$$H_l^{t+1} = \tan h[ \tag{I}$$

$$\sigma(Z_{l,1}^t) \odot S_{0,0} * H_l^t \tag{II}$$

$$+ \sigma(Z_{l,2}^t) \odot S_{0,-1} * H_l^t \tag{III}$$

$$+ \sigma(Z_{l,3}^t) \odot S_{-1,0} * H_l^t \tag{IV}$$

$$+ \sigma(Z_{l,4}^t) \odot S_{1,0} * H_l^t \tag{V}$$

$$+ \sigma(Z_{l,5}^t) \odot S_{0,1} * H_l^t \tag{VI}$$

$$+ \sigma(Z_{l,6}^t) \odot \tan h(Z_{l,7}^t)] \tag{VII}(6)$$

$\sigma(A)$ represents the application of the sigmoid function $1/(1+e^{-a})$ element wise to every element a of the tensor A. The sigmoid function may be referred to as a "squashing" function. The sigmoid function takes in an input value anywhere from $+\infty$ to $-\infty$ and squashes the input value to an output value from 0 to 1.

Tan h is also a squashing function. It also takes in an input value anywhere from $+\infty$ to $-\infty$ but the tan h function squashes the input value to an output value from $-1$ to 1.

The operator $\odot$ represents a Hadamard product operation. If, given the equation A$\odot$B for example, a Hadamard product operation between input B and input A is performed. The Hadamard product is an elementwise multiplication of each pair of elements from two identically sized inputs.

$Z_l^t$ is a tensor that contains the results 326 of the computation performed at the third layer 325 at resolution 1 and time step t. $Z_l^t$ has dimensions $N_l \times N_l \times 7 \times C_H$. Each of the seven elements of the third dimension has a specific role in the spatiotemporal gating process. The variables $Z_{l,1}^t$ through $Z_{l,7}^t$ in the equation refer to the tensor that results when one of the seven elements is selected. Each tensor associated with each of the seven elements has the dimensions $N_l \times N_l \times C_H$.

$H_l^t$ is a tensor 322 that holds an internal state for each node in the spatial lattice at resolution 1 and time step t. As described above, the internal state is dynamically updated at each time step. The tensor has the dimensions $N_l \times N_l \times C_H$. Therefore, there are $C_H$ variables describing each node at resolution 1.

$S_{\Delta x, \Delta y}$ is a spatial shifting convolution operator. It has no learnable parameters. $S_{\Delta x, \Delta y}$ allows information from the internal states of nearest neighbor nodes to be considered when determining the current internal state of a node.

Returning to the equation above, the results 326 that are stored in the tensor $Z_l^t$ are broken into seven parts. Each part represents an element in the third dimension of the tensor $Z_l^t$, as described above. Line (I) of equation (6) applies a tan h squashing function to the sum of lines II-VII of equation (6) to determine the internal state of a node at the current iteration. Line (II) of equation (6) corresponds to the possibility of copying the internal state of the node from the previous time stamp to the current time stamp, depending on the gated value. The next four lines (III-VI) $(+\sigma(Z_{l,2}) \odot S_{0,-1} * H_l^t, +\sigma(Z_{l,3}^t) \odot S_{-1,0} * H_l^t, +\sigma(Z_{l,4}^t) \odot S_{1,0} * H_l^t, +\sigma(Z_{l,5}^t) \odot S_{0,1} * H_l^t)$ each correspond to the possibility of copying the internal states of one of the nearest neighbors from the previous iteration to the internal state of the node in the current iteration. The last line (VII) corresponds to generating a completely new value and possibly setting the internal state of the node at the current iteration to the new value.

Figure 4:
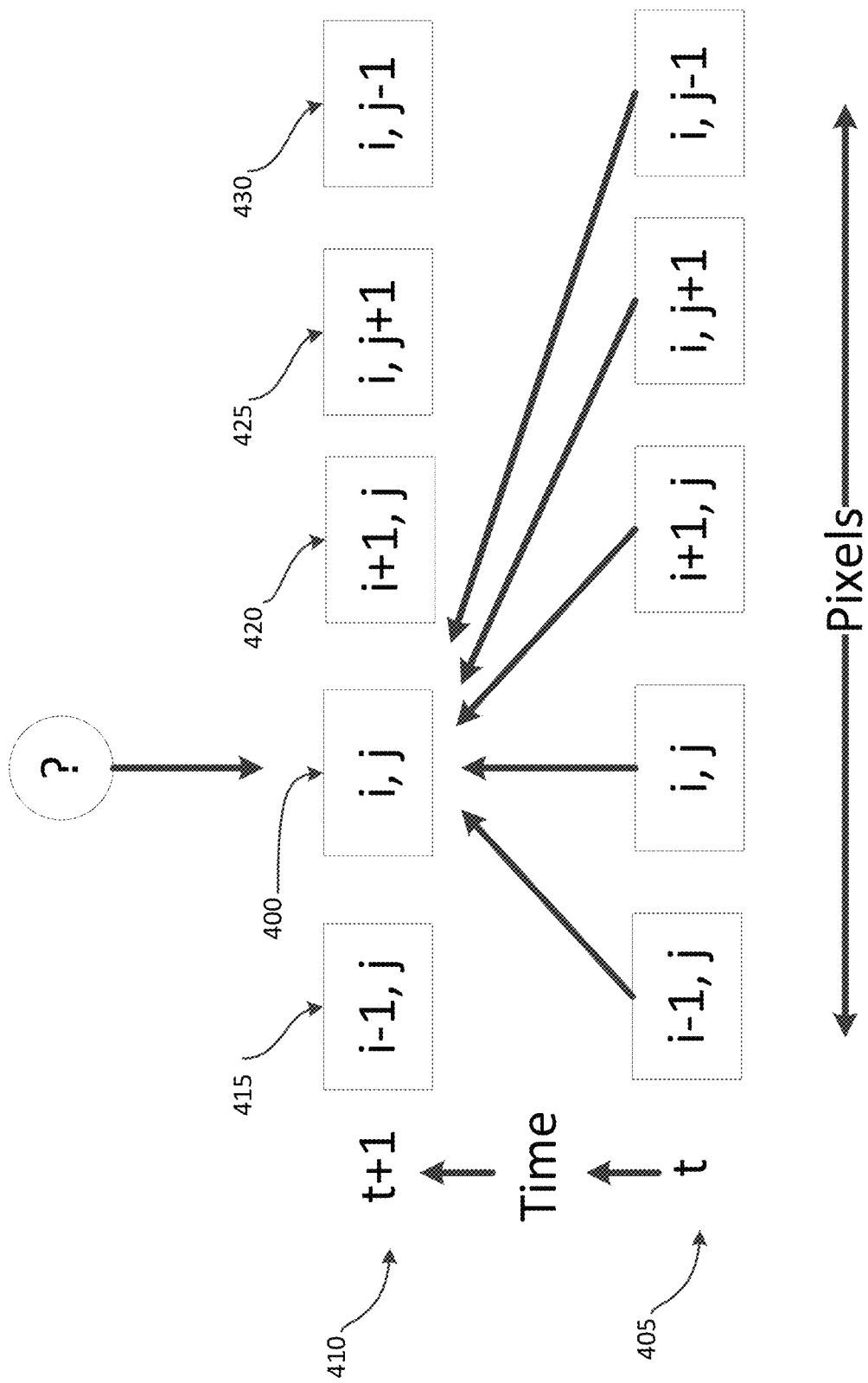
FIG. 4 illustrates an example of input to a node in a gated spatiotemporal unit.

FIG. 4 illustrates the connections between a node 400 whose internal state is being determined in a current iteration and nodes with internal states that were determined at a previous iteration. Each node is connected to nodes whose internal states were calculated at a most previous iteration of the gated spatiotemporal unit 330. Specifically, each node is connected to a node that represents its own internal state in the most previous iteration of the gated spatiotemporal unit 330 as well as nodes that represent internal states of its neighboring nodes in the most previous iteration of the gated spatiotemporal unit 330. In FIG. 4, nodes in the group 405 are nodes that are each associated with internal states that are determined in a most previous iteration of the neural network 208. Nodes in the group 410 are nodes that are associated with internal states that are determined in the current iteration of the neural network 208. As described above, each node corresponds to a pixel (or block of one or more pixels) in the input image 300. Each neighboring node of a node represents a pixel (or block of one or more pixels) that is adjacent to the pixel (or block of one or more pixels) represented by the node. For example, if a node 400 represents a pixel in the image at coordinates (i,j), then the node 400 representing the pixel at (i,j) is connected to a node 415 representing a pixel at coordinates (i−1,j) (directly to the left of the pixel at (i,j)), a node 420 representing a pixel at coordinates (i+1,j) (directly to the right of the pixel at (i,j)), a node 425 representing a pixel at coordinates (i,j+1) (directly above the pixel at (i,j)), and a node 430 representing a pixel at coordinates (i,j−1) (directly below the pixel at (i,j)). Each of the above nodes, described as being connected to the node 400 representing the pixel (i,j), are the neighboring nodes of the node 400. Therefore, the gated spatiotemporal unit 330 determines whether to set the internal state of the node 400 to the internal state of one of the nodes in the group 405.

When the internal states of the nodes in the spatial lattice of the gated spatiotemporal unit 330 converge (change less than a predetermined amount), the internal states of the nodes representing the input image 300 at the highest resolution are output to a final layer 335 of the neural network 208. The final layer 335 uses one value included in the internal state of each node to calculate the probability (for example, a value between zero and one) that the pixel that that node represents belongs to the object of interest in the input image 300. The following equation describes the operation performed in the final layer 335 to determine the probability that each pixel is a part of an object of interest:

$$Y^t = \sigma(K_1^Y * H_1^t) \quad (7)$$

$Y^t$ is a variable representing the output 305 of the neural network 208 at time step t and has dimensions $N_0 \times N_0 \times 1$ (the same dimensions as the input).

$H_1^t$ is a tensor that holds an internal state for each node in the spatial lattice at resolution 1 and time step t.

$K_1^Y$ is a variable that represents a convolution operator that preserves the dimensions of the input image data. The input image data has the dimensions $N_0 \times N_0 \times C_1$, while the output image data has the dimensions $N_0 \times N_0 \times 1$. K may represent the combination of several sequential convolution operations that are arranged as in, for example, AlexNet, DenseNet, or a range of other architectures and the learnable parameters of the convolutional operators.

In summary equation (7) applies a final convolution using $K_1^Y$ to the highest resolution internal state $H_1^t$, thereby reducing the number of input channels ($C_H$) to 1 output channel. The equation applies the sigmoid function to the results of applying a final convolution using $K_1^Y$ to the highest resolution internal state $H_1^t$, thereby squashing each value included in $Y^t$ to a value between 0 and 1. Each value in $Y^t$ between 0 and 1 corresponds to the probability that an image pixel lies inside an object of interest in the input image 300. For example, if the value produced by the sigmoid function for a single pixel is 0.5 then there is a fifty percent (50%) probability that the pixel is within the object of interest.

The neural network 208 may store generated output 305 (the calculated probabilities for each node) in an output data repository (e.g., the memory 206) or provide generated output 305 for use or consumption, such as by displaying the output 305 to a user on a display device. Regardless, the electronic processor 204 compares the probability for each pixel that the pixel is included in an object of interest to a predetermined threshold. If the probability that a pixel is a part of an object of interest is above a predetermined threshold, the electronic processor 204 determines that the pixel is a part of the object of interest.

It should be understood that, in some embodiments, in the neural network 208 described above equations (4-6) is performed for each level of representation of the input image 300 ($I_1$–$I_l$) included in the image pyramid 315. It should also be understood that while the neural network 208 is described above as propagating values over time, space, and resolutions, the neural network 208 may be modified to only propagate values over time and space.

It should also be understood that the values of the gates used to determine the internal state of each node at each iteration need not be either zero or one, but may be any value between 0 or 1 (see equation (6) above). Accordingly, in some embodiments, the updated internal state of a node may be a mixture (or, more mathematically, a linear combination) of two or more of the options described above (a value of the node from a previous iteration, values of one or more neighboring nodes from a previous iteration, and a new value of the node).

Figure 5:
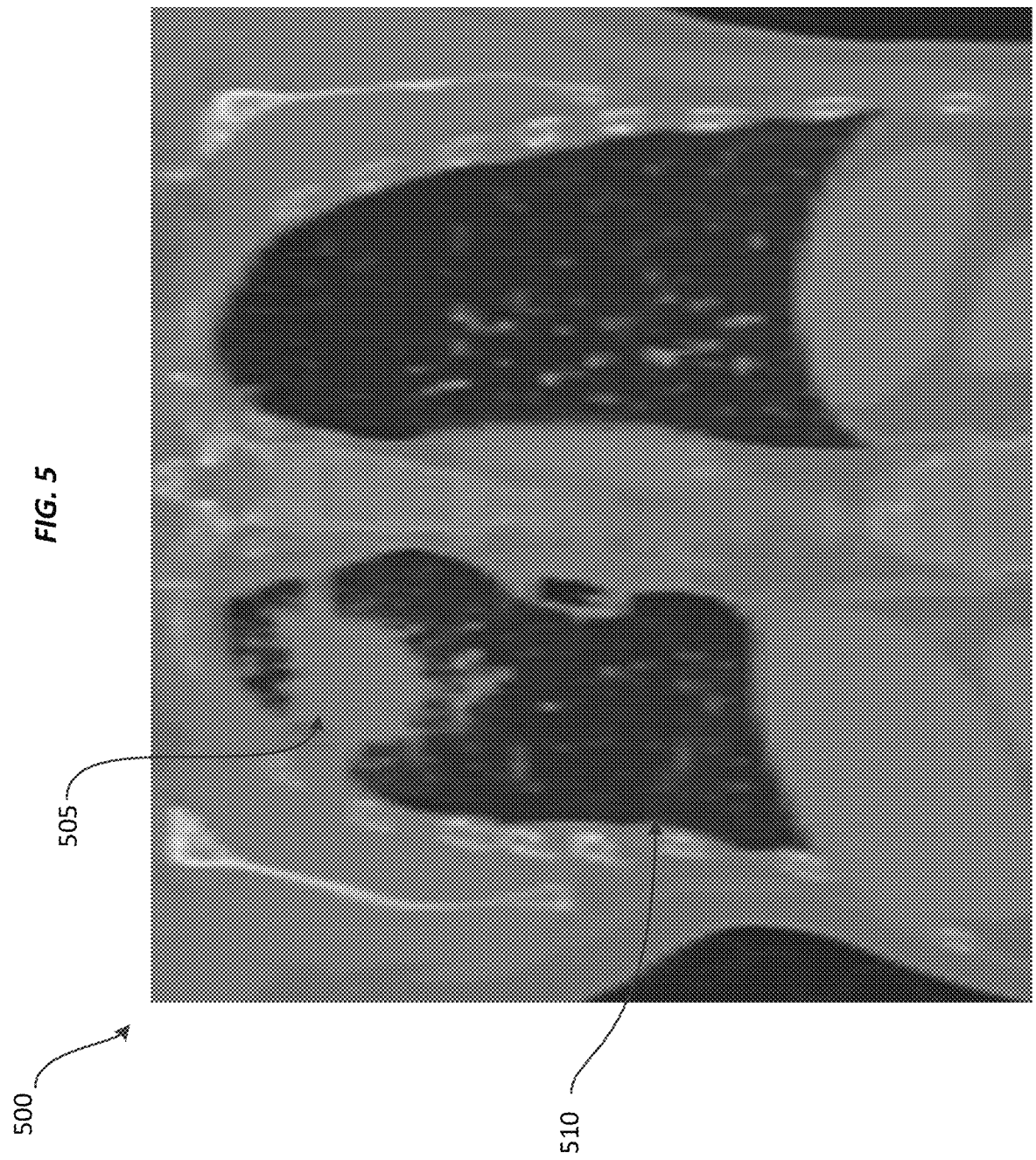
FIG. 5 illustrates an example of a medical image that the neural network of FIG. 4 receives as input.
Figure 6:
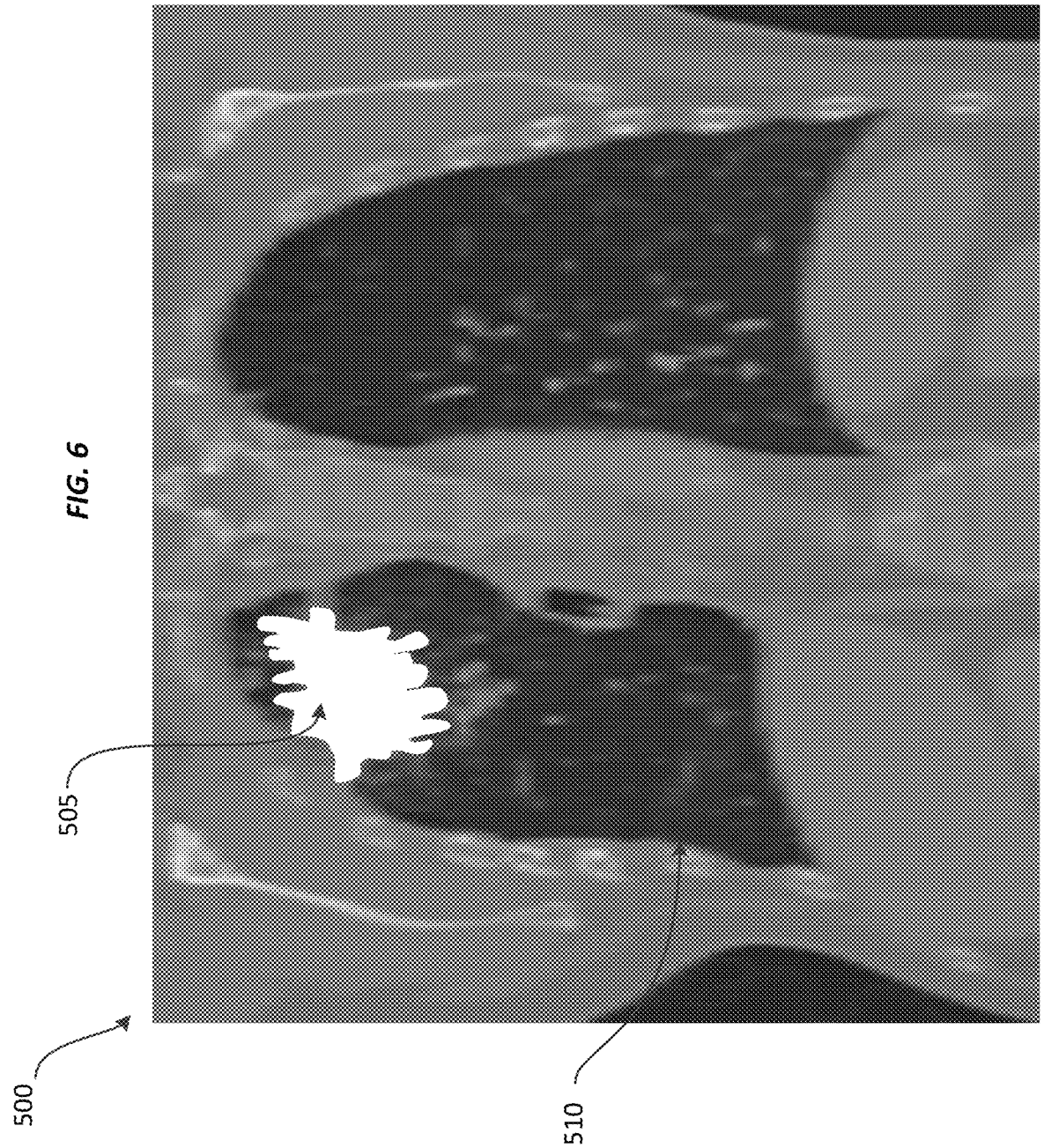
FIG. 6 illustrates an example of a region of interest that the neural network of FIG. 4 detects in the medical image of FIG. 5.

FIG. 5 and FIG. 6 provide an example of a practical application of the neural network 208. FIG. 5 illustrates an example of a medical image 500 that the neural network 208 may receive as input. The object of interest in the image 500 is a tumor 505 in a left lung 510. FIG. 6 illustrates the area of the medical image 500 that the neural network 208 identifies as an object of interest (the tumor 505). Unlike when the region growing technique is used (see FIG. 1), the boundaries of the object of interest do not extend outside of the left lung 510.

Thus, embodiments described herein provide a neutral network that includes a spatiotemporal unit. The spatiotemporal unit is a spatially extended lattice of nodes. Each node corresponds, for example, to a pixel in an image. The neural network determines an initial internal state for each node and iteratively updates the internal state for each node to produce a new internal state over and over again by propagating values over time, over space, or both and by calculating new values to represent the internal state for each node. Accordingly, as compared to other types of RNNs, such as long short term memory (LSTM) networks and gated recurrent unit (GRU) networks that iterate on one-dimensional sequences of letters or words, embodiments described herein consider the decisions of neighboring nodes when updating the internal state of each node. In particular, embodiments described herein apply both spatial and temporal dimensions. Accordingly, although the time dimension only iterates forwards, spatial gating allows spatial information to resonate back and forth over the spatial lattice for as long as needed, as new conclusions are reached in one part of the image and propagated to other parts of the image to inform decision making at those parts. Additionally, in some embodiments described herein, values in the neural network 208 may be propagated between different resolutions of the image.

The embodiments described herein are closed. In particular, the neural network 208 described herein is given all of the information about the outside world as initial input (the image needing processing) and from that point onward the neural network 208 evolves in time only according to its own internal state and rules, not taking in any further information from the outside. As such, the iteration continues until convergence, when there are no further changes to the internal state. This makes the neural network 208 like an algorithm rather than a function. In contrast, RNNs are given a new piece of the problem (e.g., one word) at each time step, so the iteration continues only as long as there is new information available.

Various features and advantages of some embodiments are set forth in the following claims.

What is claimed is:

1. A method for identifying an object of interest in a medical image, the method comprising:
    creating an image pyramid for the medical image, wherein the image pyramid includes a plurality of layers, each layer includes a plurality of values, each value represents a block of one or more pixels in the medical image, and each successive layer includes fewer values than a most previous layer;
    for each layer of the image pyramid;
        initializing internal states of nodes of a spatial lattice, wherein each node in the spatial lattice represents a block of one or more pixels in the medical image and is connected to at least one node representing a neighboring block of one or more pixels in the medical image; and
        iteratively updating, using a neural network, the internal states of the nodes in the spatial lattice using spatially gated propagation, wherein at each iteration each node updates its internal state based on at least one selected from the group consisting of a value of the node from a previous iteration, a value of a neighboring node from the previous iteration, and a new value of the node; and
    identifying the object of interest within the medical image based on the values of the nodes at a convergence of the spatial lattice having nodes representing the values included in a first layer of the image pyramid.

2. The method according to claim 1, wherein iteratively updating, using a neural network, the internal states of the nodes includes updating a value in a vector of values associated with the internal states of the nodes.

3. The method according to claim 1, the method further comprising
    performing, at each iteration for each layer of the image pyramid, a first convolution involving a first concatenation of previous internal states of the nodes representing the values included in a layer of the image pyramid and the values included in the layer of the image pyramid, and
    storing results of performing the first convolution.

4. The method according to claim 3, the method further comprising performing, at each iteration for each layer of the image pyramid, a second convolution involving a second concatenation of results of performing the first convolution for a current layer of the image pyramid, a layer of the image pyramid directly above the current layer of the image pyramid, and a layer of the image pyramid directly below the current layer of the image pyramid.

5. The method according to claim 4, wherein each node updates its internal state based on at least one selected from the group consisting of a value of the node from a previous iteration, a value of a neighboring node from the previous iteration, and a new value of the node includes using a squashing function and results of performing the second convolution.

6. The method according to claim 1, wherein creating the image pyramid includes performing convolutions on each value representing a brightness of each block of one or more pixels in the medical image, wherein each convolution involving a reduction of dimensions of input medical image data produces values that are used to represent the medical image in a next layer of the image pyramid.

7. The method according to claim 1, wherein each value representing the medical image in the first layer of the image pyramid corresponds to a pixel in the medical image.

8. The method according to claim 7, wherein identifying the object of interest within the medical image based on the values of the nodes at a convergence of the spatial lattice having nodes representing the values included in a first layer of the image pyramid includes using a final layer of the neural network to calculate a probability that each pixel in the medical image is included in the object of interest based on a value included in each vector of values associated with a node representing the values included in a first layer of the image pyramid; and
    determining, for each pixel, if the calculated probability is above a predetermined threshold.

9. The method according to claim 1, wherein the neighboring node is one selected from a group consisting of a node that represents a block of one or more pixels that is directly above, directly below, to the right of, and to the left of a block of one or more pixels represented by the node.

10. The method according to claim 1, wherein representing the medical image with fewer values creates a medical image with a lower resolution.

11. A system for determining a region of interest in an image, the system comprising
    a memory; and
    an electronic processor, connected to the memory and configured to:
        create an image pyramid for the image, the image pyramid including a plurality of layers, for each layer of the image pyramid,
  initialize internal states of nodes of a spatial lattice, wherein each node represents a block of one or more pixels in the image and is connected to at least one node representing a neighboring block of one or more pixels in the image, and
  iteratively update, using a neural network, the internal states of the nodes in the spatial lattice using spatially gated propagation; and
identify the region of interest within the image based on the internal states of the nodes at a convergence of the spatial lattice having nodes representing values included in a first layer of the image pyramid.

12. The system according to claim 11, wherein each successive layer of the plurality of layers included in the image pyramid represents the image at a lower resolution than an image represented in a most previous layer of the image pyramid.

13. The system according to claim 12, wherein the electronic processor is configured to represent the image at a lower resolution by representing the image with fewer values.

14. The system according to claim 13, wherein the electronic processor is configured to perform, at each iteration for each layer of the image pyramid, a first convolution involving a first concatenation of previous internal states of the nodes representing the values included in the layer of the image pyramid and the values included in the layer of the image pyramid, and store results of performing the first convolution.

15. The system according to claim 14, wherein the electronic processor is configured to perform, at each iteration for each layer of the image pyramid, a second convolution involving a second concatenation of results of performing the first convolution for a current layer of the image pyramid, a layer of the image pyramid directly above the current layer of the image pyramid, and a layer of the image pyramid directly below the current layer of the image pyramid.

16. The system according to claim 15, wherein the electronic processor is configured to update the internal state based on at least one selected from the group consisting of a value of the node from a previous iteration, a value of a neighboring node from the previous iteration, or a new value of the node by using a squashing function and results of performing the second convolution.

17. The system according to claim 12, wherein the electronic processor is further configured to perform, in the first iteration, convolutions on each value representing a brightness of each block of one or more pixels in the image, wherein each convolution involving a reduction of dimensions of input image data produces values that are used to represent the image in a next layer of the image pyramid.

18. The system according to claim 11, wherein the electronic processor is configured to update the internal states of the nodes by, at each iteration, deciding for each node whether to maintain a value of the node from a previous iteration, to set a value of the node to a value of a neighboring node from a previous iteration, or set a new value of the node.

19. The system according to claim 18, wherein the neighboring node is one selected from the group consisting of a node that represents a block of one or more pixels in the image that is directly above, directly below, to the right of, and to the left of the block of one or more pixels in the image represented by the node.

20. The system according to claim 11, wherein the electronic processor is configured to iteratively update, using a neural network, the internal states of the nodes by updating a value in a vector of values associated with the internal states of the nodes.

21. The system according to claim 11, wherein the electronic processor is configured to identify an object of interest within the image based on the values of the nodes at a convergence of the spatial lattice having nodes representing values included in a first layer of the image pyramid by using a final layer of the neural network to calculate a probability that each pixel in the image is included in the object of interest based on each vector associated with a node representing the values included in a first layer of the image pyramid, and
  determining, for each pixel, if the calculated probability is above a predetermined threshold.

22. Non-transitory computer-readable medium storing instructions that, when executed with an electronic processor, perform a set of functions, the set of functions comprising:
  creating an image pyramid for an image, wherein the image pyramid includes a plurality of layers, each layer includes a plurality of values, each value represents a block of one or more pixels in the image, and each successive layer includes fewer values than a most previous layer;
  for each layer of the image pyramid;
    initializing internal states of nodes of a spatial lattice, wherein each node represents a block of one or more pixels in the image and is connected to at least one node representing a neighboring block of one or more pixels in of the image; and
    iteratively updating, using a neural network, the internal states of the nodes in the spatial lattice using spatially gated propagation, wherein at each iteration each node updates its internal state based on at least one selected from the group consisting of a value of the node from a previous iteration, a value of a neighboring node from the previous iteration, or a new value of the node; and
  identifying an object of interest within the image based on the values of the nodes at a convergence of the spatial lattice having nodes representing the values included in a first layer of the image pyramid.

23. The non-transitory computer-readable medium according to claim 22, wherein iteratively updating, using a neural network, the internal states of the nodes includes updating a value in a vector of values associated with the internal states of the nodes.

24. The non-transitory computer-readable medium according to claim 22, wherein identifying an object of interest within the image based on the values of the nodes at a convergence of the spatial lattice having nodes representing the values included in a first layer of the image pyramid includes using a final layer in the neural network to calculate a probability that each pixel in the image is included in the object of interest based on the vector associated with a node representing the values included in a first layer of the image pyramid; and
  determining, for each pixel, if the calculated probability is above a predetermined threshold.

* * * * *